United States Patent [19]

Shull

[11] Patent Number: 4,701,445

[45] Date of Patent: Oct. 20, 1987

[54] EASILY DISPERSIBLE AGGLOMERATED HYGROSCOPIC COMPOSITIONS

[75] Inventor: James J. Shull, Tucson, Ariz.

[73] Assignee: Shulcon Industries, Inc., Tucson, Ariz.

[21] Appl. No.: 630,285

[22] Filed: Jul. 12, 1984

[51] Int. Cl.[4] .......................................... A61K 31/715
[52] U.S. Cl. ...................................... 514/57; 514/54; 514/60
[58] Field of Search ..................... 424/180; 514/54, 57, 514/60

[56] References Cited

U.S. PATENT DOCUMENTS

| 3,328,848 | 7/1967 | Magid | 167/82 |
|---|---|---|---|
| 3,639,637 | 2/1972 | Campbell | 424/346 |
| 3,911,114 | 10/1975 | Cardon | 424/128 |
| 4,009,268 | 2/1977 | Cardon et al. | 424/180 |
| 4,010,262 | 3/1977 | Cardon et al. | 424/180 |
| 4,120,952 | 10/1978 | Cardon | 424/180 |
| 4,198,400 | 4/1980 | Biegler | 424/180 |

FOREIGN PATENT DOCUMENTS 2097804 11/1982 United Kingdom .

OTHER PUBLICATIONS

Vogel Chemical Abstracts vol. 97, 1982 No. 133608d.
Solka-Floc® Cellulose Fibre Filter Aids Technical Bulletin SF-12, Grefco, Inc. (Subsidiary of General Refactories Co.), pp. 4-6 and attachment.
Avicel® Microcrystalline Cellulose product description, FMC Corporation Food & Pharmaceutical Products, Philadelphia, Pa. 19103.
Alpha-Cel® Brochure, International Filler Corporation, North Tonawanda, New York 14120, pp. 2-3 and attachments.

Primary Examiner—Johnnie R. Brown
Assistant Examiner—Elli Peselev
Attorney, Agent, or Firm—Marshall, O'Toole, Gerstein, Murray & Bicknell

[57] ABSTRACT

Dispersion of agglomerated hydroscopic powders such as agglomerated pregelatinized starch antidiarrheal agent is enhanced by the admixture of fibrous cellulose. Preferred methods and compositions include admixtures of agglomerated pregelatinized starch with from about 6 to 10 weight percent fibrous cellulose having average fibre lengths of about 100 microns or greater.

9 Claims, 1 Drawing Figure

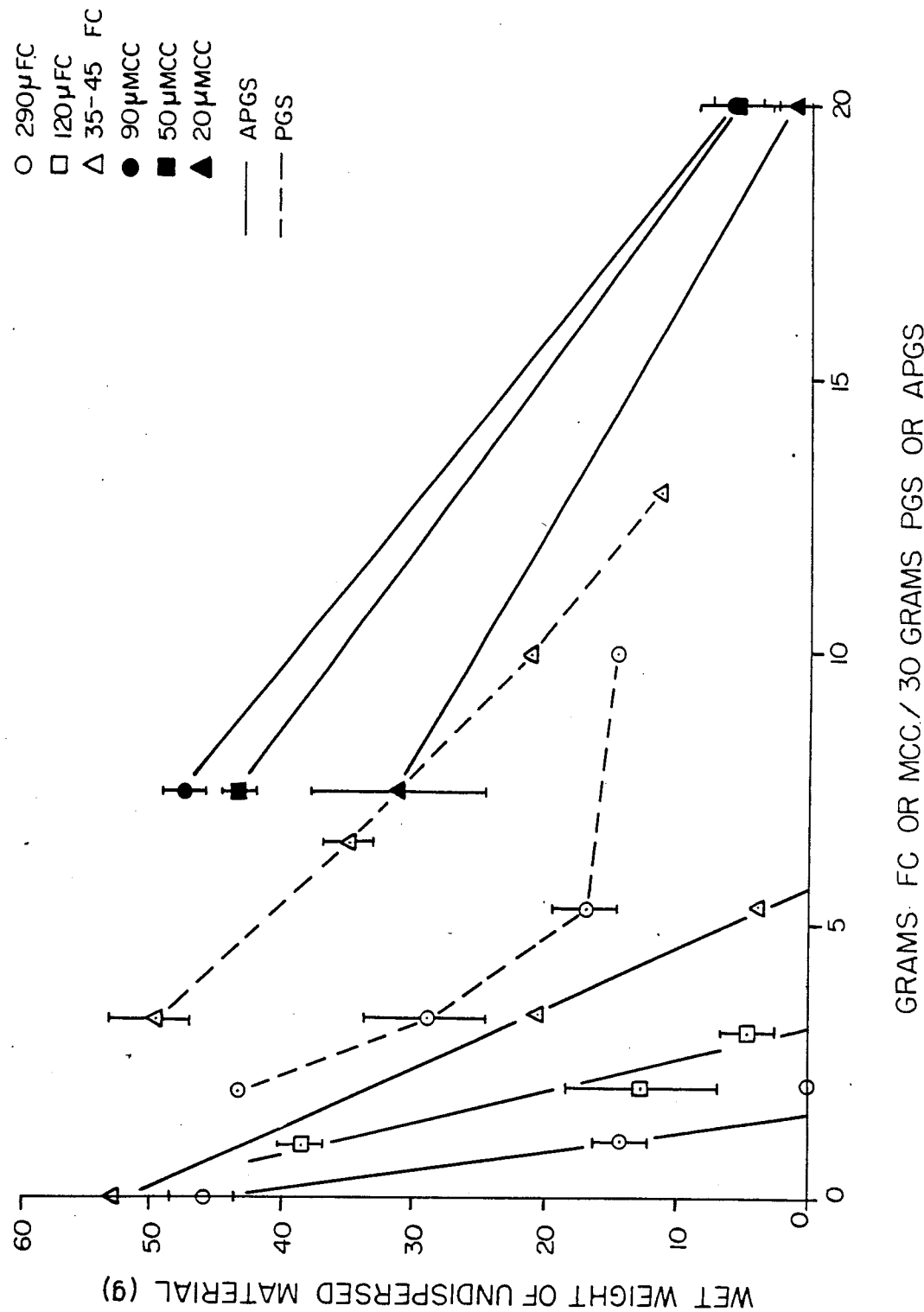

EASILY DISPERSIBLE AGGLOMERATED HYGROSCOPIC COMPOSITIONS

BACKGROUND OF THE INVENTION

The present invention relates generally to improving the dispersibility of agglomerated hygroscopic powders such as pregelatinized starch, whole milk, skim milk, whole milk replacer, whey powders, powdered yeast and fish protein extracts, animal feeds, baby foods, and maltodextrines. More specifically, in its presently preferred form, the invention relates to methods for enhancing the dispersibility of agglomerated pregelatinized starch and to resulting compositions of easily dispersible agglomerated pregelatinized starch.

Mammals, including ruminants such as cattle and sheep and monogastric animals such as pigs, horses and human beings, often suffer from diarrhea or "scours". It has been reported that diarrhea is a serious health problem for adult cattle (U.S. Pat. No. 3,911,114) and causes high mortality rates for neonatal calves (U.S. Pat. No. 4,009,268). Monogastric animals, including pigs, horses and humans, are also reported to suffer significantly from diarrhea (U.S. Pat. No. 4,120,952), i.e., one-fifth of newborn pigs which contract diarrhea die without treatment (U.S. Pat. No. 4,010,262).

The above-mentioned patents disclose methods for treating diarrhea in the animal by administering oral dosages of an aqueous mixture of an antidiarrheal agent, pregelatinized starch (PGS). Typically the methods involve mixing a dry pregelatinized starch commercial product with water and forcing the resultant PGS solution or paste down a tube inserted in the animal's throat. (See, e.g., U.S. Pat. Nos. 3,911,114 and 4,010,262.) Other disclosed methods include mixing the pregelatinized starch with other liquids, such as milk, and feeding the mixture to the animal. (See, U.S. Pat. No. 4,120,952).

Although PGS appears to be an effective antidiarrheal agent, mixing pregelatinized starch with liquids is difficult due to the intrinsic properties of the starch. As produced commercially, pregelatinized starch is an extremely hygroscopic powder. Characteristic of hygroscopic powders, PGS disperses with difficulty in aqueous media. If added directly to such media too quickly and without sufficient agitation, the dry starch powder becomes encapsulated by stiff paste into balls of material which are very difficult to disperse. This incomplete dispersion makes the mixture more difficult to administer to the patient to the point that force-feeding may be required. Incomplete dispersion also means that a greater amount of pregelatinized starch may be required to achieve the desired antidiarrheic effect than if complete dispersal had been obtained.

The wettability of pregelatinized starch can be enhanced by agglomerating the particles of pregelatinized starch through controlled addition of water and redrying. The result is a coarse powder, agglomerated pregelatinized starch (APGS), that wets more readily in aqueous media and disperses more easily than pregelatinized starch. However, substantial care is still required when mixing agglomerated pregelatinized starch in water to avoid formation of lumps of stiff paste which resist dispersion.

In application of pregelatinized starch compositions such as PGS or APGS as an antidiarrheal, unskilled persons are expected to mix the compositions into water or aqueous suspensions and administer the solution orally to the patient. In intensive livestock production enterprises, however, instructions to take special precautions to mix medications slowly and carefully are often unheeded. To be accepted for routine use, a pregelatinized starch antidiarrheal product must be readily dispersible in aqueous media without the need for exceptional precautions for mixing, and with great margin for error. Thus formulations of pregelatinized starch compositions with mixing qualities superior to both PGS and APGS compositions presently available are required.

It is generally known in the art that the dispersibility of a composition can be improved through incorporation of a "dispersant" component which readily absorbs water. Many compounds are known to act as dispersants for certain compositions including raw starch used in tableting as an excipient and as a dispersant for PGS, and FDA approved anticaking agents for animal feeds such as polysorbate-60 and polysorbate-80. Sodium aluminum silicate may similarly be employed as an anticaking agent. U.S. Pat. No. 3,332,848 (Col. 1, line 68 to Col. 2, line 4) discloses incorporation of microcrystalline cellulose into multiple vitamin tablets to enhance the dispersibility of the tablets in aqueous vehicles. U.S. Pat. No. 3,696,637 discloses enhancing the dispersibility of estrogen in aqueous solutions by admixing microcrystalline cellulose with the hormone prior to mixing with water.

Although dispersants are generally known as a class, the choice of a dispersant is dependent primarily on the composition sought to be dispersed and the context within which the composition is intended to be used. In the present case, the dispersant must interact with a hygroscopic powder, APGS, intended to be ingested by livestock on a large-scale basis, and by human beings. It is therefore essential that the dispersant be non-toxic, inert and inexpensive. It is also preferred that the dispersant be a constituent of the normal diet of the patient. Further restrictions exist with respect to the nature and amount of dispersants that may be fed to livestock raised for human consumption, e.g., the U.S. Food & Drug Administration would be expected to require extensive retesting of PGS if the amount of dispersant in the antidiarrheal compositions were to exceed 10%. These and other regulatory restrictions would likely exist with respect to agglomerated hygroscopic powders such as milk, baby food, protein extracts and the like which are intended for direct human consumption.

As noted above, microcrystalline cellulose has been reported to function as a dispersant for estrogen in aqueous mixtures administered to cattle, (U.S. Pat. No. 3,639,637), and as a dispersant in vitamin tablets (U.S. Pat. No. 3,332,848). Microcrystalline cellulose is purified alpha cellulose particles prepared from processing alpha cellulose from fibrous plant materials. It is an inert, organic material and is a commercial product sold under various tradenames including Avical (American Viscose Division, FMC Corp.), as an excipient and extender in pharmaceutical tableting. (Avicel ® Sales Brochure).

Although microcrystalline cellulose initially appears attractive as a possible dispersant for APGS, actual testing consistent with this suggestion has proven unsuccessful. As indicated in more detail below, applicant prepared mixtures of various proportions of microcrystalline cellulose and the antidiarrheal APGS starch. It was found that a minimum of 35% to 40% microcrystalline cellulose was required to significantly improve the dispersibility of APGS. The size of the microcrystalline cellulose particles was also found to influence dispersibility, the smaller sized particles (20 microns) being more effective than the larger 50 micron and 90 micron particles. At concentrations of about 35% microcrystalline cellulose, the cost of the mixture was three times that of APGS alone.

There continues to exist, therefore, a need in the art for a method of enhancing the dispersibility of agglomerated hygroscopic powders such as APGS and for easily dispersible APGS antidiarrheal compositions.

BRIEF SUMMARY OF THE INVENTION

The present invention provides novel methods for enhancing the dispersibility of agglomerated hygroscopic powders such as agglomerated pregelatinized starch (APGS) which comprises admixing the powder with a dispersionally effective amount of fibrous cellulose having an average fibre length of greater than 100 microns.

Presently preferred dispersionally effective amounts of fibrous cellulose for use in these methods are those providing, on a dry weight basis, about 10 weight percent or less (and more preferably 6 to 7 weight percent) of the total weight of the admixture. Preferred fibrous cellulose materials for use in the invention have an average fibre length of between about 120 to 290 microns, and most preferably, an average fibre length of about 290 microns.

Exemplary easily dispersible hygroscopic powder compositions according to the invention include admixtures of APGS and dispersionally effective amounts of fibrous cellulose having an average fibre length of greater than 100 microns. Preferred compositions include admixtures of, on a dry weight basis, about 90 to 94 percent APGS and about 6 to 10 percent fibrous cellulose having an average fibre length of between 120 and 290 microns. Presently most highly preferred compositions are those which include 93 to 94 percent APGS and 6 to 7 percent fibrous cellulose with a 290 micron average fibre length.

Compositions of the invention possess enhanced dispersibility in aqueous media. Such enhanced dispersion is readily achieved without the need for careful mixing steps or elaborate mixing equipment. Compositions according to the invention flow in live-bottom automated packaging equipment, further facilitating their use on a large-scale basis.

Commercially available fibrous cellulose may be employed in the present invention without the need for treatment of fibres to render them hydrophobic, in distinction to use of lypophilized fibrous cellulose food thickening agents as disclosed in U.S. Pat. No. 4,198,400.

Other aspects and advantages of the invention will become apparent upon consideration of the following detailed description wherein FIG. 1 graphically illustrates the enhanced dispersibility of APGS consistent with methods and compositions according to the invention.

DETAILED DESCRIPTION

EXAMPLE 1

Dispersion of Agglomerated Pregelatinized Starch By Admixture of Fibrous Cellulose Samples of dry fibrous cellulose were obtained from Grefco, Inc., Torrence, Calif. The samples, Solka-Floc TM BW-100 (fibre length 35–45 microns) and Solka-Floc TM KS-1016 (fibre length 290 microns), were tested for their effectiveness in aiding dispersion of dry powdered agglomerated pregelatinized starch (APGS) Diamylex ® (Shulcon Industries, Phoenix, Ariz.), as follows.

Each fibrous cellulose sample was mixed with 30 grams of the agglomerated pregelatinized starch in concentrations of 10, 15 and 20% fibrous cellulose, and the dry fibrous cellulose/APGS mixtures were tested for dispersion in water at room temperature according to the following protocol:

Each mixture, containing 30 g of agglomerated pregelatinized starch and the appropriate quantity of fibrous cellulose was added to the quiescent surface of 1 liter of water in a cylindrical container 6 inches in diameter and 6¾ inches tall. The dry mixture was added suddenly and allowed to stand without agitation for 30 seconds. The contents of the can were then swirled 100 times in 30 seconds and then poured through a piece of ⅛ inch mesh hardware cloth. The sides of the container were washed with a small amount of water and the washings were poured over any retained material on the hardware cloth. Material retained on the hardware cloth was transferred to a tared container and weighed. The mixtures tested were ordered randomly for the testing sequence using a random numbers table generated by a Hewlett-Packard Model 97 Desk Calculator.

The results of the experiment are set forth in Table I, below.

TABLE I

| % of Fibrous Cellulose in APGS | Wet Weight of Solids Retained on Hardware Cloth (in grams) Fibrous Cellulose Fiber Length (Ave.) 35–45μ | 290μ |
|---|---|---|
| 0 | 53.1 | 58.7 |
| 10 | 20.8 | 0 |
| 15 | 3.7 | 0 |
| 20 | 0 | 0 |

The results set forth in Table I indicate that fibrous cellulose is an effective dispersant and that, of the types tested, the material having the longest (e.g., 290 micron) average fibre length is the most effective on a weight basis. The effective concentration of 290 micron fibres is 10 percent or less, on a dry weight basis, of the total admixture.

The following Example illustrates an experiment examining the dispersion effect of 290 micron fibrous cellulose on agglomerated pregelatinized starch at lower concentrations of the fibrous cellulose and in warm water.

EXAMPLE 2

Dispersion Effect of 290μ Fibrous Cellulose on APGS

Solka-Floc TM fibrous cellulose KS-1016 (290μ) was mixed with agglomerated pregelatinized starch (APGS) in amount of 1, 2 and 3 grams of fibrous cellulose per 30 grams APGS and tested against the dispersibility of APGS alone in random order according to the protocol of Example 1, except the water temperature was raised to 115°–117° F.

The results of this experiment are set forth in Table III below.

TABLE II

| | Wet Weight of Solids Retained on Hardware Screen (in grams) | | | |
|---|---|---|---|---|
| | Grams of 290 Micron Fibrous Cellulose/30 g APGS | | | |
| Replicate # | 0 | 1 | 2 | 3 |
| 1 | 43.7 | 16.0 | 0 | 0 |
| 2 | 45.8 | 12.1 | 0 | 0 |
| 3 | 48.5 | 14.5 | 0 | 0 |
| (Means | 46.0 | 14.2 | 0 | 0) |
| S.D. | ±2.41 | ±1.97 | 0 | 0 |

The results set forth in Table II show that 6.3% (i.e., 2 g/32 g mixture×100%) of Solka-Floc ™ KS-1016 fibrous cellulose having an average fibre length of 290 microns in an admixture with APGS effectively acts as an aid in dispersing the APGS in water. There appears to be little influence of temperature on the test results using this system. When mixed with an adequate quantity of 290 micron fibre length fibrous cellulose to permit complete dispersion of the APGS, the mixture floats on the surface of the water until a concerted effort is made to mix it. The dispersion effectiveness of the 290 micron fibrous cellulose may be partially attributable to its extreme buoyancy, inhibiting premature wetting of the starch.

The following example illustrates testing of the dispersion effect of fibrous cellulose having average fibre lengths of 120 microns on agglomerated pregelatinized starch.

EXAMPLE 3

Dispersion Effect of 120μ Fibrous Cellulose on APGS

Solka-Floc ™ KS-1040, with an average fiber length of 120 microns was tested as a dispersant for agglomerated pregelatinized starch (APGS), employing 1, 2, or 3 g of the 120 micron fibrous cellulose per 30 g of APGS. The test system used is described in Example 1. The results obtained are set forth in Table III below.

TABLE III

| | Wet Weight of Solids Retained on Hardware Cloth (in grams) | | |
|---|---|---|---|
| | Grams of 120 Micron Fibrous Cellulose/30 g APGS | | |
| Replicate # | 1 | 2 | 3 |
| 1 | 36.8 | 10.6 | 3.8 |
| 2 | 38.4 | 19.0 | 6.8 |
| 3 | 40.3 | 8.2 | 2.8 |
| (Means | 38.5 | 12.6 | .47) |
| S.D. | ±1.75 | ±5.67 | ±2.08 |

These results indicate that fibrous cellulose having a fibre length of about 120 microns is an effective dispersant of APGS at amounts of about 10 weight percent.

The following Example illustrates the dispersion effect of fibrous cellulose on unagglomerated pregelatinized starch (PGS).

EXAMPLE 4

Dispersion of Pregelatinized Starch By Fibrous Cellulose

Tests were performed to evaluate the dispersibility of unagglomerated pregelatinized starch (PGS) with fibrous celluloses of two different fiber lengths, 290 microns (Solka-Floc ™ KS-1016) and 35–45 microns (Solka-Floc ™ BW-100). The test methods of Example 1 were followed. The results are set forth below.

TABLE IV

| | Wet Weight of Solids Retained on Hardware Cloth (in grams) | | |
|---|---|---|---|
| g Fibrous | | Fibre Length of Fibrous Cellulose | |
| Cellulose/30 g PGS | Replicate | 35–45μ | 290μ |
| 2.00 | 1 | — | 43.2 |
| 3.33 | 1 | 47.6 | 29.4 |
| | 2 | 53.5 | 23.9 |
| | 3 | 48.7 | 33.4 |
| | (Means | 49.93 | 28.9) |
| | (S.D. | ±3.1 | ±4.8) |
| 5.3 | 1 | — | 19.2 |
| | 2 | — | 14.4 |
| | 3 | — | 17.1 |
| | Mean | — | 16.9 |
| | S.D. | — | 2.4 |
| 6.6 | 1 | 37.1 | — |
| | 2 | 34.0 | — |
| | 3 | 33.7 | — |
| | (Mean | 34.93 | —) |
| | S.D. | 1.9 | — |
| 10 | 1 | 21 | 14.5 |
| 12.9 | 1 | 11.5 | — |

As indicated by the above results, 290 micron and 35–45 micron fibrous cellulose present in amounts of 10 weight percent were ineffective in dispersing PGS. Much higher amounts of even the 290 micron long fibrous cellulose were required to disperse the 30 g sample of PGS.

The following Example illustrates the effect of microcrystalline cellulose of varying particle size on the dispersibility of agglomerated pregelatinized starch.

EXAMPLE 5

Dispersion of Agglomerated Pregelatinized Starch by Microcrystalline Cellulose

After preliminary tests to establish the range of concentration of microcrystalline cellulose needed to effect some degree of dispersion of agglomerated pregelatinized starch (APGS), three grades of microcrystalline cellulose were tested for effectiveness in enhancing dispersion of APGS in water. The test method used in described in Example 1. Avicel ® microcrystalline cellulose products PH-105 (particle size, 20 microns), PH-101 (particle size, 50 microns) and PH-102 (particle size, 90 microns) were employed. The results are set forth in Table V below.

TABLE V

| | Wet Weight of Solids Retained on Hardware Cloth (in grams) | | | |
|---|---|---|---|---|
| g Microcrystalline Cellulose/ | | Microcrystalline Cellulose Particle Size | | |
| 30 g APGS | Replicate | 20μ | 50μ | 90μ |
| 20 | 1 | 0 | 5.2 | 8 |
| | 2 | 0 | 7.6 | 2.7 |
| | 3 | 3 | 3.8 | 6.1 |
| | (Means | 1.0 | 5.5 | 5.6) |
| | S.D. | 1.7 | 1.9 | 2.7 |
| 7.5 | 1 | 28.7 | 44.1 | 48.8 |
| | 2 | 38.7 | 43.6 | 45.6 |
| | 3 | 26.3 | 41.6 | 47.4 |
| | (Means | 31.2 | 43.1 | 47.3) |
| | S.D. | ±6.6 | ±1.3 | ±1.6 |

The results indicate that even at very high amounts (i.e., 20%) microcrystalline cellulose does not significantly disperse APGS. The results also show that the smaller the size of the microcrystalline cellulose particle, the greater its ability to disperse APGS.

The following Example illustrates the effectiveness of preferred methods and compositions according to the invention in treating diarrheic mammals.

EXAMPLE 6

Treatment of Diarrheic Mammals With Fibrous Cellulose/APGS Admixtures

The therapeutic effectiveness of the admixture of 6.3% fibrous cellulose (Solka-Floc ™ KS-1016, 290μ) and APGS (Diamylex ®, Shulcon Industries, Phoenix, Ariz.) was evaluated in a clinical field setting. Two hundred (200) diarrheic calves were treated with the admixture according to the package instructions specifying that one packet (32 g) of the admixture be dissolved in one quart or greater volume liquid feed and administered to each calf twice daily at normal feeding times for two days promptly upon the first occurrence of diarrheic symptoms. The effectiveness of this treatment was evaluated against treatment of 50 diarrheic calves using 30 g of PGS alone in liquid feed performed as part of the regulatory approval of PGS as an antidiarrheal. The results of both treatments are set forth in Table VI, below.

TABLE VI

Therapeutic Effectiveness of a Dispersible Fibrous Cellulose/APGS Mixture

|  | PGS | 6.3% Fibrous Cellulose (290μ) in APGS |
|---|---|---|
| Total # of Calves Treated | 50 | 200 |
| % Responding to Treatment* | 72 | 80 |

*Returned to normal without further or auxiliary treatment.

As indicated in Table VI, 80% of the diarrheic calves treated with the 290μ fibrous cellulose/APGS admixture responded to the treatment and returned to normal without the need for additional treatment, a response which is similar to the 72% response rate obtained with PGS alone.

EXAMPLE 7

Dispersion Effect of Fibrous Cellulose on Antidiarrheal/Nutrient Compositions and Agglomerated Antidiarrheal/Nutrient Compositions The dispersion effect of Solka-Floc ™ KS-1016 (290μ) fibrous cellulose upon antidiarrheal compositions including nutritional salts and sugar was evaluated according to the method of Example 1. The first antidiarrheal compositions examined included the following ingredients.

| NaCl | 9.4% |
|---|---|
| KCl | 3.1% |
| NaHCO₃ | 6.7% |
| Dextrose | 53.4% |
| PGS | 21.2% |
| KS-1016 | 6.2% |
|  | 100.0% |

One batch (70.42 g) was prepared by mixing all the above ingredients except the fibrous cellulose and agglomerating the mixture. KS-1016 fibrous cellulose (6.2%) was then admixed to the composition.

A second antidiarrheal composition was prepared according to the above formula except that 21.2% APGS was substituted for the PGS and no agglomeration of this APGS/nutritional salts and sugar admixture was conducted. An equal amount (6.2%) of KS-1016 was then admixed with this antidiarrheal composition. Both compositions were tested for dispersibility in water according to the method of Example 1. The results are set forth in Table VII below.

TABLE VII

| | Sample I | | Sample II | |
|---|---|---|---|---|
| Antidiarrheal Composition | Dry Weight (g) | Wet Weight Retained on Screen (g) | Dry Weight (g) | Wet Weight Retained on Screen (g) |
| APGS, Nutritional Mixture and 290μ Fibrous Cellulose | 37.5 | trace | 37.5 | 0.5 |
| Agglomerated PGS/Nutritional Mixture and 290μ Fibrous Cellulose | 37.5 | 0 | 37.5 | 0 |
| Agglomerated PGS/Nutritional Mixture Without 290μ Fibrous Cellulose | 35.2 | 8.5 | 35.2 | 12.3 |

As indicated by the above results, the presence of 6.2% of 290μ fibrous cellulose significantly increased the dispersibility of the agglomerated PGS/nutritional salts and sugar mixture. Additionally, it was observed that fibrous cellulose also significantly improved the dispersion of APGS and non-agglomerated nutritional ingredients including the hygroscopic dextrose component.

FIG. 1 graphically illustrates the enhanced dispersibility of agglomerated pregelatinized starch according to the methods and compositions of the present invention. The data for Examples 1 to 6 pertaining to fibrous cellulose admixtures with APGS are indicated in FIG. 1 as follows. The dispersibility of APGS as influenced by varying amounts of: (1) 290 micron fibrous cellulose (FC) is shown by the solid line connecting open circles (—⊙—); (2) 120 micro fibrous cellulose is shown by the solid line connecting open squares (—□—); and (3) the 35-45 micron fibrous cellulose is shown by the solid line connecting open triangles (—△—). The effect of 290 micron and 35-45 micron fibrous cellulose on unagglomerated PGS dispersion is indicated by the broken lines connecting the open circles (--⊙--) and triangles (--△--), respectively. The data set forth in Example 5 relating to the dispersion effect of microcrystalline cellulose (MCC) of varying particle sizes and amounts on APGS is indicated in FIG. 1 by the solid lines connecting the filled circles (—●—, 90 micron), filled squares (—■—, 50 micron), and filled triangles (—▲—20 microns).

As indicated in FIG. 1, 35-40% microcrystalline cellulose is required in a microcrystalline cellulose/APGS admixture to effect significant dispersion of the antidiarrheal. At this concentration the cost of the microcrystalline cellulose would triple the cost of the antidiarrheal composition. The results also indicate that the smaller particles of microcrystalline cellulose (20 microns) were more effective in dispersing APGS than the larger particles (50 and 90 microns).

Unexpectedly, applicants have discovered that fibrous cellulose having certain fibre lengths greatly enhance the dispersibility of APGS. As shown in FIG. 1, the amounts of fibrous cellulose required to achieve complete dispersion of APGS is much less than that of microcrystalline cellulose. With materials of similar particle size (35–45 micron fibrous cellulose v. 50 micron microcrystalline cellulose), about one-fourth the amount of the fibrous cellulose was required to obtain complete dispersion of APGS than with the microcrystalline cellulose. In addition, it was discovered that the dispersibility of APGS was strongly influenced by *increasing* fiber length of the cellulosic material added. In contrast to the results obtained with microcrystalline cellulose, where smaller particles produced better dispersibility, increase in fiber length dramatically improved dispersibility of mixtures of fibrous cellulose with APGS. The longest fibrous cellulose materials tested (290 microns) were about 10 times more effective than the most effective (20 micron particle size) microcrystalline cellulose in enhancing dispersion.

Fibrous cellulose having average fiber lengths of approximately 100 microns or greater were effective in eliciting total dispersion of APGS mixtures with concentrations of fibrous cellulose of about 10% or less. At these low concentrations, the inert organic dispersant fibrous cellulose has no effect on the antidiarrheal properties of pregelatinized starch, and the additional cost of the fibrous cellulose material is well within tolerable limits.

Fibrous cellulose having fibers of 100 microns or larger are also more effective than shorter fiber length material in enhancing dispersibility of PGS in water, although, as expected, the concentration of fibrous cellulose required was greater than with APGS. The magnitude of the effect of fiber length was also substantially greater when APGS was employed in the mixture. The quantity of fibrous cellulose required for complete dispersion of PGS was reduced by half when the fiber length was increased from 35–45 microns to 290 microns. The same change in fiber length resulted in a 75% reduction in fibrous cellulose concentration with APGS. As indicated in Example 6, actual clinical field tests utilizing fibrous cellulose/APGS admixtures according to the invention proved effective in treatment of diarrheic calves, eighty percent of the diarrheic calves so treated returning to normal after two days of treatment.

While the method of Example 2 utilizing the composition disclosed therein of about 93–94 weight percent APGS and 6–7 weight percent fibrous cellulose having an average fibre length of about 290 microns is clearly the presently most preferred and thoroughly tested procedure of the invention, it is expected that equally effective results may be obtained through use of other APGS compositions using lesser amounts of fibrous cellulose having fibre lengths of greater than 100 microns consistent with applicant's teachings.

It is also expected that the dispersibility of other selected agglomerated hygroscopic powders alone or in conjunction with nutritional ingredients such as those set forth in Example 7 may be enhanced by admixing them with dispersionally effective amounts of fibrous cellulose having fibre lengths of greater than 100 microns.

Consistent with the foregoing disclosure, numerous modifications and variations in the practice of the invention are expected to occur to those skilled in the art. Consequently, only those limitations as appear in the appended claims should be placed on the invention above described.

What is claimed is:

1. An easily dispersible antidiarrheal composition consisting essentially of an admixture of an antidiarrheally effective amount of agglomerated pregelatinized starch and a dispersionally effective amount of fibrous cellulose having fibres of an average length of about 100 microns to about 290 microns.

2. The composition according to claim 1 wherein said fibrous cellulose comprises, on a dry weight basis, about 10 weight percent or less of the total composition.

3. The composition according to claim 2 wherein said fibrous cellulose comprises, on a dry weight basis, from about 6 to about 10 weight percent of said composition.

4. The composition according to claim 1 wherein said fibrous cellulose has an average fibre length of between about 120 microns to about 290 microns.

5. The composition according to claim 4 wherein said fibrous cellulose has an average fibre length of about 290 microns.

6. An easily dispersible antidiarrheal composition consisting essentially of an admixture of agglomerated pregelatinized starch and a dispersionally effective amount of fibrous cellulose, said fibrous cellulose comprising, on a dry weight basis, about 10 weight percent or less of said admixture and having an average fibre length of from about 100 to about 290 microns.

7. The composition according to claim 6 wherein said fibrous cellulose comprises, on a dry weight basis, from about 6 to about 10 weight percent of the total admixture.

8. The composition according to claim 7 wherein said fibrous cellulose has an average fibre length of about 290 microns.

9. An easily dispersible antidiarrheal composition consisting essentially of, on a dry weight basis, about 93–94 weight percent of agglomerated pregelatinized starch and about 6–7 weight percent of fibrous cellulose having an average fibre length of about 290 microns.

* * * * *